(12) United States Patent
Shoelson et al.

(10) Patent No.: US 8,445,467 B2
(45) Date of Patent: May 21, 2013

(54) REDUCING RISK OF TYPE 2 DIABETES (T2D)

(75) Inventors: Steven Shoelson, Natick, MA (US); Allison B. Goldfine, Wayland, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 717 days.

(21) Appl. No.: 12/298,627

(22) PCT Filed: Apr. 27, 2007

(86) PCT No.: PCT/US2007/067615
§ 371 (c)(1), (2), (4) Date: Jun. 25, 2009

(87) PCT Pub. No.: WO2007/127913
PCT Pub. Date: Nov. 8, 2007

(65) Prior Publication Data
US 2009/0298796 A1    Dec. 3, 2009

Related U.S. Application Data

(60) Provisional application No. 60/796,155, filed on Apr. 28, 2006.

(51) Int. Cl.
*A61K 31/60* (2006.01)
(52) U.S. Cl.
USPC .......................................... 514/159; 514/866
(58) Field of Classification Search
USPC ................................................ 514/159, 866
See application file for complete search history.

(56) References Cited

U.S. PATENT DOCUMENTS

| | | | |
|---|---|---|---|
| 6,043,233 A | 3/2000 | Garvey et al. | |
| 6,355,666 B1 * | 3/2002 | Lai et al. | 514/411 |
| 2011/0021468 A1 | 1/2011 | Shoelson et al. | |

OTHER PUBLICATIONS

Silver et al., "FDA-Approved Dose of Salsalate Improves Glucose and Lipid Metabolism in Type 2 Diabetes", Diabetes, vol. 53, No. Suppl. 2, p. A161 (Jun. 2004).*
Goldfine et al., 'The Effects of Salsalate on Glycemic Control in Patients with Type 2 Diabetes,' Ann Intern Med., 152:346-357 (2010).
Yin et al., "The anti-inflammatory agents aspirin and salicylate inhibit the activity of IκB kinase-β," Nature 396:77-80 (1998).
Amos et al., Diabet. Med., "The Rising Global Burden of Diabetes and its Complications: Estimates and Projections to the Year 2010," 5:S1-85 (1997).
April et al., Arthritis Rheum., "Does the Acetyl Group of Aspirin Contribute to the Anti-inflammatory Efficacy of Salicylic Acid in the Treatment of Rheumatoid Arthritis," 19:20-28 (1990).
Atkinson, Clin. Ther., "Assessment of Salsalate, a Nonacetylated Salicylate, in the Treatment of Patients with Arthritis," 17:827-837 (1995).
Cai et al., Nature Med., "Local and Systematic Insulin Resistance Resulting from Hepatic Activation of IKK-β and NF-κB," 11:183-190 (2005).
*Diagnosis and Classification of Diabetes Mellitus*, Diabetes Care, 28:S37-S42.
Ford et al., JAMA, "Prevalence of the Metabolic Syndrome Among U.S. Adults," 287:356-359 (2002).
Hundal et al., Clin. Invest., "Mechanism by which High-Dose Aspirin Improves Glucose Metabolism in Type 2 Diabetes," 109:1321-1326 (2002).
King et al., Diabetes Care, "Global Burden of Diabetes, 1995-2025: Prevalence, Numerical Estimates, and Projections," 21:1414-1431 (1998).
Matthews et al., Diabetologia, "Homeostasis Model Assessment: Insulin Resistance and β-Cell Function from Fasting Plasma Glucose and Insulin Concentrations," 28:412-419 (1985).
Meigs, Current Opin. Endocrinol. Diabetes, "Definitions and Mechanisms of the Metabolic Syndrome," 13:103-110 (2006).
Mokdad et al., Diabetes Care, "Diabetes Trends in the U.S.: 1990-1198," 23:1278-1283 (2000).
Mokdad et al., JAMA, "The Continuing Epidemic of Obesity in the United States," 284:1650-1651 (2000).
Mokdad et al., JAMA, "The Continuing Epidemics of Obesity and Diabetes in the United States," 286:1195-1200 (2001).
Mokdad et al., JAMA, "Prevalence of Obesity, Diabetes, and Obesity-Related Health Risk Factors, 2001," 289:76-79 (2003).
Reaven, Diabetes, "Role of Human Insulin Resistance in Human Disease," 37:1595-1607 (1988).
Shoelson et al., Int. J. Obes. Relat. Metab. Disord., "Inflammation and the IKKβ/IκB/NF-κB Axis in Obesity- and Diet-Induced Insulin Resistance," 3:S49-S52 (2003).
Silver Robert J. et al., "FDA-approved dose of salsalate improves glucose and lipid metabolism in type 2 diabetes", 53:A161 (2004).
Stevenson et al., "Salsalate Cross-Sensitivity in Aspirin-Sensitive Patients with Asthma," J. Allergy. Clin. Immunol., 86:749-758 (1990).
Wallace et al., Diabetes Care, "Use and Abuse of HOMA Modeling," 27:1487-1495 (2004).
Wild et al., Diabetes Care, "Global Prevalence of Diabetes: Estimates for the Year 2000 and Projections for 2030," 27:1047-1053 (2004).

(Continued)

*Primary Examiner* — Kevin E Weddington
(74) *Attorney, Agent, or Firm* — Pierce Atwood LLP; Kevin M. Farrell; David J. Wilson (57) ABSTRACT

This invention relates to methods for reducing chronic subacute inflammatory states associated with obesity and improve glycemia, thereby preventing or delaying the development of type 2 diabetes (T2D) in obese subjects, or subjects with the metabolic syndrome, using non-acetylated forms of salicylate, e.g., salsalate or trilisate.

25 Claims, 4 Drawing Sheets

OTHER PUBLICATIONS

Yuan et al., Sci., "Reversal of Obesity- and Diet-Induced Insulin Resistance with Salicylates or Targeted Disruption of Ikkβ," 293:1673-1677 (2001).

Silver, et al.; Salsalate, A Novel Treatment for Type 2 Diabetes; Endocrinology Practice Journal; vol. 10, No. 1; 2004; pp. 43-44 Abstract 126.

Aldhahi, et al.; High Dose Salsalate Improves Glucose Metabolism in Humans with Insulin Resistance; The Endocrine Society; Jun. 2003; p. 99 Abstract OR 29-1.

Fleischman, et al.; Salicylates improve Glucose Metabolism and Inflammation in Obese non-diabetic Young Adults; Endocrine Society; Jun. 2006; 2 pages.

Harrison, et al.; High-Pressure Liquid Chromatographic Determination of Salicylsalicylic Acid, Aspirin, and Salicylic Acid in Human Plasma and Urine; Journal of Pharmaceutical Sciences; vol. 69, No. 11; Nov. 1980; pp. 1268-1271.

Marette; Molecular mechanisms of inflammation in obesity-linked insulin resistance; International Journal of Obesity; vol. 27; 2003; pp. S46-S48.

Abraham, et al.; Salsalate exacerbation of chronic renal insufficiency. Relation to inhibition of prostaglandin synthesis; vol. 147, No. 9; Sep. 1987; pp. 1674-1676 (Abstract only).

Perseghin, et al.; Cellular mechanism of insulin resistance: potential links with inflammation; International Journal of Obesity; vol. 27; 2003; pp. S6-S11.

Khan, et al.; Relevance of Platelet-independent Effects of Aspirin to Its Salutary Effect in Atherosclerosis-related Events; Journal of Atherosclerosis and Thrombosis; vol. 12; Apr. 19, 2005; pp. 185-190.

Oeth, et al.; Salicylates Inhibit Lipopolysaccharide-Induced Transcriptional Activation of the Tissue Factor Gene in Human Monocytic Cells; Blood; vol. 86, No. 11; Dec. 1, 1995; pp. 4144-4152.

Fleischman, et al.; Salsalate Improves Glycemia and Inflammatory Parameters in Obese Young Adults; Diabetes Care, vol. 31, No. 2; Feb. 2008; pp. 289-294.

Goldfine, et al.; A Targeting Inflammation Using Salsalate to Prevent Diabetes; 71st Scientific Sessions; 50-OR; 2011.

Documents exchanged with the European Patent Office in the corresponding European application (No. EP077614402), (2011).

Goldfine, et al.; Use of Salsalate to Target Inflammation in the Treatment of Insulin Resistance and Type 2 Diabetes; vol. 1, No. 1; May 1, 2008; pp. 36-43.

Williams, et al.; Salsalate Kinetics in Patients with Chronic Renal Failure Undergoing Hemodialysis; vol. 39, No. 4; Apr. 1986; pp. 420-424 (Abstract only).

* cited by examiner

REDUCING RISK OF TYPE 2 DIABETES (T2D)

CROSS-REFERENCE TO RELATED APPLICATIONS

This application is the U.S. national stage under 35 USC §371 of International Application Number PCT/US2007/067615, filed on Apr. 27, 2007, which claims the benefit under 35 USC 119(e) to U.S. Provisional Patent Application Ser. No. 60/796,155, filed on Apr. 28, 2006, the entire contents of which are hereby incorporated by reference.

FEDERALLY SPONSORED RESEARCH OR DEVELOPMENT

This invention was made with Government support media Grant Nos. R01 DK57129, K23-DKG2795, and P50-HL083813, awarded by the National Institutes of Health. The Government has certain rights in the invention.

TECHNICAL FIELD

This invention relates to methods for reducing chronic subacute inflammatory states associated with obesity and improve glycemia, thereby preventing or delaying the development of type 2 diabetes (T2D) in obese subjects using non-acetylated forms of salicylate, e.g., salsalate.

BACKGROUND

Obesity is a major risk factor for hyperglycemia and diabetes, as well as other dysmetabolic states. Obesity and type 2 diabetes are occurring at epidemic rates in the United States and worldwide (National Diabetes Data Group, Diabetes in America. 2 ed, USA: National Institutes of Diabetes and Digestive Diseases, National institutes of Health, 1994; Mokdad et al., Diabetes Care 23(9): 1278-12 S3 (2000); Mokdad et al., JAMA 284(13): 1650-1651 (2000); Mokdad et al, JAMA 286(10): 1195-1200 (2001); Mokdad et al., JAMA 289(1):76-79 (2003)). In the year 2000, an estimated 2.9 million individuals died from diabetes-related causes (Roglic et al., Diabetes Care 28:2130-2135, 2005) and the global burden of diabetes is estimated to doable over the nest 25 years (King et al. Diabetes Care 21:1414-1431, 1998; Amos et al., Diabet Med 14 Suppl 5:S1-85, 1997; Wild et al, Diabetes Care 27:1047-1053, 2004 in parallel with the rise in obesity. Therefore, there is an urgent need for effective interventions to prevent the development of type 2 diabetes in obese populations. The importance of the standard initial treatment of lifestyle modification for both obesity and diabetes is well recognized. However, the generally disappointing long-term results of these treatment modalities have led to increased interest in pharmaceutical intervention.

SUMMARY

The present inventors have discovered that administration of high doses of non-acetylated forms of salicylate, e.g., salsalate or trilisate, is useful for preventing (i.e., reducing the risk of developing) or retarding the development of type 2 diabetes (T2D), or for preventing or retarding the inflammatory processes that lead to the development of T2D, in overweight and obese subjects, and subjects with the metabolic syndrome.

In one aspect, the invention provides methods for preventing or delaying the development of type 2 diabetes (T2D) in a subject with a body mass index (BMI) of $\geq 25$, The methods include determining whether the subject has a BMI of $\geq 25$, and if the subject has a BMI$\geq 25$, then administering, to the subject a therapeutically effective amount of a non-acetylated form of salicylate, thereby preventing or delaying the development of T2D in the subject. In some embodiments, the subject is selected on the basis that they have a BMI of $\geq 25$.

In another aspect, the invention provides methods for preventing or delaying the development of type 2 diabetes (T2D) in a subject who has metabolic syndrome. The methods include determining whether die subject has metabolic syndrome, and if the subject has metabolic syndrome, then administering to the subject a therapeutically effective amount of a non-acetylated form of salicylate, thereby preventing or delaying the development of T2D in the subject. In some embodiments, the subject is selected on the basis that they have the metabolic syndrome.

In some embodiments, the subject is selected based on one or more of the following criteria: the subject is at risk for T2D; the subject has tasting glucose levels of 100-125; the subject has a 2-Hour plasma-glucose result in a Oral Glucose Tolerance Test (OGTT) of 140-498 mg/dL; and/or the patent has a BMI of $\geq 25$, e.g., $\geq 30$; and then the patient is selected for treatment for preventing or delaying of T2D with a non-acetylated form of salicylate.

In some embodiments, the methods include informing the subject that the purpose of the treatment is for preventing or delaying of T2D.

In some embodiments, at the time of administration of one or more of the first, second, or third dose of a non-acetylated form of salicylate, the subject is not being treated for diabetes, e.g., have not been prescribed or are not taking insulin, meglitinides, biguanides, thiazolidinediones, or alpha-glucosidase inhibitors.

In some embodiments, the methods further include testing the subject for T2D after treatment with a non-acetylated form of salicylate to prevent or delay T2D has began, and optionally, if the patient develops T2D, administering to the subject a treatment for T2D, wherein the treatment is other than a non-acetylated form of salicylate.

In some embodiments, the methods include determining whether the subject has a BMI of $\geq 30$, and if the subject has a BMI$\geq 30$, then selecting the subject on the basis that the subject has a BMI of $\geq 30$, and administering to the subject a therapeutically effective amount of a non-acetylated form, of salicylate, thereby preventing or delaying the development of T2D in the subject.

In some embodiments, the non-acetylated form of salicylate is salsalate or trilisate. In some embodiments, a therapeutically effective amount of a non-acetylated form of salicylate is about 3-4.5 g/day e.g., 3 g/day, 3.5 g/day, 4 g/day, or 4.5 g/day.

In some embodiments, the subject is not suffering from pain. In some embodiments, the subject is not being administered a non-acetylated form of salicylate for the treatment of pain, e.g., pain from inflammation or a joint disorder or rheumatoid arthritis (RA).

In some embodiments, determining whether the subject has a BMI of $\geq 25$ includes determining the subject's weight, determining the subject's height, and calculating the subject's BMI using the subject's weight and height in the following formula:

weight in kilograms divided by height in meters squared ($BMI$=kg/m$^2$)

In some embodiments, determining whether the subject has metabolic syndrome comprises determining whether the subject has at least three of the following: abdominal obesity, lasting blood triglycerides, low blood HDL, high blood pressure, and elevated fasting glucose.

In some embodiments, the methods further include determining whether the subject has T2D, and if the subject does not have T2D, then administering a therapeutically effective amount of a non-acetylated form of salicylate. Determining whether the subject has T2D can include, for example, administering one or more of a fasting plasma glucose test, wherein a result of 125 mg/dL or more indicates that the subject has T2D; and a 2-Hour plasma glucose result in a Oral Glucose Tolerance Test (OGTT), wherein a result of 199 mg/dL or indicates that the subject has T2D; and a blood glucose lest, wherein a level of more than 200 mg/dL indicates that the subject has T2D.

In some embodiments, the methods include administering a test, e.g., one or more of a subject fasting plasma glucose test, an OGTT, and/or a blood glucose test, to determine a value for the tested parameter in the subject; comparing the subject's value with a preselected standard or reference value for the same parameter; and if the subject's value has a predetermined relationship to the standard or reference value, then selecting the subject for administration of a non-acetylated form of salicylate, e.g., as described herein.

As used herein, "preventing" means effecting a statistically significant decrease in a subject's risk of developing T2D. Preventing does not require a complete, 100% decrease in risk of developing T2D in treated subjects. Thus the methods described herein can be used to reduce the likelihood that a subject will develop T2D.

In addition, the methods described herein include methods for instructing a care giver on the administration of a non-acetylated form of salicylate for the prevention of T2D (e.g., to reduce the risk of T2D) in a subject. The methods include instructing said care giver to determine a value in the subject for one or more of BMI, a subject fasting plasma glucose test, an OGTT, and/or a blood glucose test, and/or determining whether the subject has T2D or metabolic syndrome. If one or more of the values are met as described herein (e.g., BMI of $\geq 25$ or $\geq 30$; fasting glucose levels of 100-125; and/or a 2-Hour plasma glucose result In an OGTT of 140-198 mg/dL), or if the subject has metabolic syndrome, then said care giver is instructed to administer, provide, or prescribe a non-acetylated form of salicylate to the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety, in case of conflict, the present specification, including definitions, will control.

Other features and advantages of the invention will be apparent from the following detailed description and figures, and from the claims.

DESCRIPTION OF DRAWINGS

FIG. 1A is a bar graph illustrating changes in glycemia in the subject population. Fasting glucose (left), post oral glucose challenge glucose area under the curve (AUG) (middle), and glycated albumin (right) were reduced in salsalate treated subjects when compared to placebo. Black bar salsalate, Grey bar placebo

DETAILED DESCRIPTION

The present inventors have discovered mat administration of high doses of non-acetylated forms of salicylates can reduce the chronic subacute inflammatory state associated with obesity and Improve glycemia, and inhibit the pathogenesis of type 2 diabetes. Therefore, the present methods include the systemic inhibition of inflammation by administration of high doses of non-acetylated forms of salicylate, e.g., salsalate, for preventing or retarding development of T2D, in subjects who are overweight or obese, and subjects with the metabolic syndrome.

General Methodology

The methods described herein, in general include administering (e.g., orally administering) systemic doses of non-acetylated forms of salicylate, e.g., salsalate, diflunisal, or trilisate (e.g., choline-magnesium trilisate (CMT)), Salsalate is currently commercially available under the following brand names: Argesic®-S; Disalcid®; Mono-Gesic®; Salflex®; and Salsitab®, and is presently prescribed in relatively low doses to relieve, mild pain, to reduce fever, and to reduce the pain and inflammation (swelling) caused by arthritis or other inflammatory conditions. The conventional dosage is 3000 mg daily, given orally in divided doses as follows: 1) two doses of two 750 mg tablets: 2) two doses of three 500 mg tablets/capsules; or 3) three doses of two 500 mg tablets/capsules. In contrast, the present methods generally include the administration of doses over 3000 mg per day, e.g., about 3-4.5 g/day, e.g., 3 g/day, 3.5 g/day, 4 g/day, or 4.5 g/day. In general, the dose will be the highest dose that does not cause Intolerable side effects, e.g., tinnitus and headache, in a subject In some embodiments, the methods include administering a first dose, e.g., the highest dose, e.g., 4.5 g/day, for a selected period of time, e.g., two, force, four, five, six, seven, or more days, and determining whether the subject experiences one or more intolerable side effects, e.g., tinnitus and/or headache. If the subject experiences an intolerable side effect, the dose is then decreased, e.g., by 500 mg, for a selected period of time, and the determination of the presence of side effects is repeated. This can be repeated until a dose level is reached at which the subject does not experience any intolerable side effects.

In some embodiments, the methods described herein include determining whether a subject is overweight or obese, i.e., has a body mass index (BMI) of $\geqq 25$ or above, e.g., 25-29 (overweight) or 30 or above (obese), and selecting the patient if they are overweight or obese (e.g., selecting the subject on the basis that they are overweight or obese). Once such a determination has been made, the present methods include systemic administration of high doses, e.g., 3-4.5 g/day, of non-acetylated forms of salicylate, e.g., salsalate or trilisate, to the subject, to thereby prevent the onset of type 2 diabetes (T2D).

In some embodiments, the methods described herein include determining whether a subject has the metabolic syndrome, as described herein, and selecting the patient if they have the metabolic syndrome (e.g., selecting die subject on the basis that they have the metabolic syndrome). Once such a determination has been, made, the present methods include systemic administration of high doses, e.g., 3-4.5 g/day, of non-acetylated forms of salicylate, e.g., salsalate or trilisate, to subjects who have the metabolic syndrome, to thereby treat the metabolic syndrome and prevent the onset of type 2 diabetes (T2D).

The subjects treated by the methods described herein do not have diabetes, i.e., are not diabetic. A person who is not diabetic has one or more of a Fasting Plasma Glucose Test result of 125 mg/dL or less; a 2-Hour Plasma Glucose Result in a Oral Glucose Tolerance Test of 199 mg/dL or less; and blood glucose level of less than 200 mg/dL. The subjects treated by the methods described herein are not being treated for diabetes, e.g., have not been prescribed or are not taking insulin, meglitinides, biguanides, thiazolidinediones, or alpha-glucosidase inhibitors.

In some embodiments of the methods described herein, the subjects are pain free, e.g., do not have joint pain, pain from, inflammation, or rheumatoid arthritis, e.g., are not taking (or have not been prescribed) a non-acetylated forms of salicylate for the treatment of pain. Thus, the methods described herein include the systemic administration of high doses of salicylates in obese, non-diabetic subjects who are pain free, to prevent foe development of diabetes.

Pharmaceutical Compostions

The methods described herein can include the administration of non-acetylated forms of salicylate, e.g., salsalate and trilisate, in pharmaceutical compositions. Such compositions typically include the compound (i.e., as an active agent) and a pharmaceutically acceptable carrier. As used herein, "pharmaceutically acceptable carriers" includes saline, solvents, dispersion media, coatings, antibacterial and antifungal agents, isotonic and absorption delaying agents, and the like, compatible with, pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Salsalate

Salsalate (salicylsalicylic acid or 2-hydroxybenzoE acid, 2-carboxyphenyl ester) is a dimer of salicylic acid; its structural formula is shown below.

Chemical Structures;

Salsalate

In some embodiments, the salsalate used is DISALGID® (3M Pharmaceuticals), AMIGBSIC® (Amide Pharmaceutical Inc.), ARGESIC-SA® (Econo Med), MARTHRITIC® (Marnel), MONO-GESIC®, SALSITAB®, or SALFLEX®), or a generic, e.g., as are available from Cameo Pharmaceutical Laboratories Ltd., or Pliva.

Trilisate

Trilisate (choline magnesium trisalicylate) is freely soluble in water. The absolute structure of choline magnesium trisalicylate is not known at this time. Choline magnesium trisalicylate has a molecular formula of $C_{26}H_{29}O_{10}NMg$, and a molecular weight of 539.8. When dissolved in water, trilisate appears to form 5 ions (one choline ion, one magnesium ion, and three salicylate ions).

Body Mass Index (BMI)

BMI is determined by weight relative to height, and equals a person's weight in kilograms divided by height in meters squared. ($BMI=kg/m^2$). Accepted interpretations are given in Table 1.

TABLE 1

| Category | BMI |
| --- | --- |
| Underweight | $\leqq 18.5$ |
| Normal weight | 18.5-24.9 |
| Overweight | 25-29.9 |
| Obese | $\geqq 30$ |

Thus the methods described herein can include determining a subject's height (e.g., by measuring the subject or reviewing the subject's medical history), determining a subject's weight (e.g., by weighing the subject or reviewing the subject's medical history), and calculating BMI from the values determined thereby. Alternatively, the methods described herein can include reviewing a subject's medical history to determine their BMI (e.g., where the BMI has already been calculated.

The Metabolic Syndrome

In some embodiments, the methods include determining whether a subject has the metabolic syndroms, and selecting the subject if they do have the metabolic syndrome, then systemically administering a high dose of a non-acetylated form of salicylate, e.g., salsalate or trilisate. Determining whether a subject has the metabolic syndrome can include reviewing their medical history, or ordering or performing such tests as are necessary to establish a diagnosis.

The metabolic syndrome, initially termed Syndrome X ((Reaven, Diabetes 37(12): 1595-1607 (1988)), refers to a clustering of obesity, dyslipiderma, hypertension, and insulin resistance, All components of She metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mg/dL) and/or elevated fasting glucose (e.g., greater than or equal to 110 mg/dL). In some embodiments, levels of these criteria may be higher or lower, depending on the subject; for example, In subjects of Asian ancestry; see, e.g., Meigs. "Definitions and Mechanisms of the Metabolic Syndrome." Current Opinions in Endocrinology and Diabetes, 13(2): 103-110 (2006). A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA 28(3):356-359 (2002)). Insulin resistance is now felt to be central in foe pathogenesis of these related disorders. Recently, a central role for inflammation has been postulated in this cluster of diseases.

EXAMPLES

The invention is further described in the following examples, which do not limit the scope of the invention described in the claims.

Example 1

Salicylates Improve Glucose Metabolism in Obese Non-Diabetic Young Adults

Recent studies suggest an important role for Inhibitor kappa B kinase beta/Nuclear Factor-Kappa B (IKKβ/NF-κB) signaling pathway in the pathogenesis of diet-induced insulin resistance (Yuan et ah. Science 293, 1673-167 (2001); Cai et al, Nature Medicine 11, 183-190 (2005); Shoelson et al., Int. J Obes Relat Metab Disord. 27 Suppl 3:849-S52 (2003)). High doses of salicylates have been shown to inhibit IKKβ/NF-κB activity and improve Insulin sensitivity, Salsalate, a non-acetylated dimmer of salicylate, is an equipotent inhibitor of IKKβ/NF-κB compared to aspirin, but a much weaker inhibitor of cyclooxygenase enzymes and therefore clinically safer.

The ability of high doses of systemic salsalate to reduce systemic inflammation and improve metabolic parameters was investigated in a double-masked placebo controlled trial of 20 overweight non-diabetic adults (age: 24 yrs±1, gender 17F/3M, BMI 38 kg/m²±2), evaluated at baseline and after one month of dally administration of oral salsalate 4 g or placebo.

Subjects

Subjects were under 30 years old, and obese as defined by a body mass Index (BMI) of ≧ 30 kg/m² Participants were excluded for recent blood donation, change in weight of more than 5% in the preceding six months or use of medication known to alter weight, acute febrile illness, biochemical evidence of renal or hepatic dysfunction, aspirin allergy, history of gastritis or gastrointestinal bleeding, current medications known to altar glucose metabolism, or diabetes mellitus based on screening evaluation. Female participants were excluded for pregnancy, lactation, or lack of current use of a hormonal or barrier contraceptive method.

Participants were instructed to consume a standard high-carbohydrate diet (250-300 grams/day) and abstain from strenuous exercise for three days prior to undergoing, baseline and final evaluations. Subjects were additionally instructed not to alter dietary or exercise habits daring the study Blood pressure was measured twice with the patient supine for 10 minutes. Fasting lipids and cytokines were measured, and oral glucose tolerance tests (OGTT) were performed with glucose, insulin, C-peptide and free fatty acid levels measured prior to and 30, 60, 90 and 120 minutes after 75-gram glucose load. All subjects were non-diabetic based on current American Diabetes Association guidelines (Diagnosis and Classification of Diabetes Mellitus. Diabetes Care 28:S37-S42 (2005)). AUC data were calculated by triangulation. Insulin resistance was determined using homeostasis model assessment (HOMA-IR) for insulin and C-peptide as described using the modified formula:

$$\text{HOMA-IR}_{C\text{-}peptide} = (\text{fasting } C\text{-peptide} * \text{fasting glucose})/22.5$$

See, e.g., Matthews et al, Diabetologia 28:41.2-419 (1985); Wallace et al., Diabetes Care 27; 1487-4495 (2004).

27 subjects were enrolled In the study. Que subject became in-eligible after blood donation following screening evaluation. Three subjects withdrew consent due to transportation, work and school issues and were considered non-informative; of these two bad been randomized to receive placebo and one to salsalate. No data had been obtained after the screening evaluation. Three subjects were withdrawn due to rash, and are discussed in the section on safety Twenty subjects completed the protocol, and are included in data analysis.

20 participants completed the protocol. Subject baseline characteristics were similar (Table 1) and included a female predominance in both groups. Likewise, ethnicity of the two groups was similarly diverse. Ail participants had normal fasting glucose values. Three subjects (2 in placebo group and 1 in. treatment group) had baseline 120 minute OGTT glucose values consistent with impaired glucose tolerance. No subject had diabetes mellitus at baseline.

TABLE 1

Baseline Subject Characteristics

| | Salsalate Therapy | Placebo |
|---|---|---|
| Gender | 1M/8F | 2M/9F |
| Ethnicity | 5W/3H/1B | 5W/1H/4B/1other |
| Age (years) | 23.5 ± 1.1 | 24.1 ± 1.0 |
| BMI (kg/m2) | 36.3 ± 2.2 | 38.9 ± 2.5 |
| Current smoking | 3 of 9 | 2 of 11 |
| Cholesterol (mmol/L) | 4.0 ± 0.3 | 4.6 ± 0.2 |
| Triglycerides (mmol/L) | 1.0 ± 0.1 | 1.1 ± 0.2 |
| Systolic BP | 121 ± 4 | 123 ± 4 |
| Diastolic BP | 67 ± 3 | 71 ± 3 |
| Fasting glucose (mmol/L) | 5.0 ± 0.2 | 4.8 ± 0.1 |
| 120 minute glucose (mmol/L) | 6.7 ± 0.4 | 6.8 ± 0.4 |

There were no significant differences in the baseline characteristics between the salsalate and placebo groups. (W=white, non hispanic, H=Hispanic, B=African-american, BMI=body mass index).

After completion of baseline assessments, subjects were randomized to receive salsalate, 4.0 grams daily (Caraco Pharmaceutical laboratories Ltd., Detroit, Mich.), or placebo for 4 weeks at which time an end of treatment evaluation was performed, Starting doses were selected based on tolerability data in patients with arthritis (April et al. Arthritis Rheum, 19:20-28 (1990)). A dose reduction plan was determined a priori with a reduction of 500 mg for symptoms related to salicylate use, such as tinnitus or headache. Compliance was evaluated with blood salicylate levels.

In treated participants, mean serum salicylate levels were in the established therapeutic range in rheumatology practice (0.7-2.2 mmol/L), 1.35*0.18 mmol/L at 2 weeks and 1.23±0.25 mmol/L at 4 weeks. Salicylate levels were undetectable in placebo treated persons. There were so significant changes in weight, systolic or diastolic blood pressure, or standard lipid profiles in either group.

Assays

Glucose was measured by glucose oxidation, cholesterol and HDL by cholesterol esterase assay, triglycerides via hydrolysis to glycerol and FFA (Beckman Synchron CX3delta and CX9, Beckman Coulter, Brea, Calif.), and glycohemoglobin by HPLC (TOSHO 2.2™, Tosoh Bioscience, San Francisco, Calif.). Immunoassays were performed in duplicate on serum specimens by commercial assay including RIA for insulin and C-peptide (Diagnostic Systems Laboratories, Webster, Tex.), and adiponectin (Linco research, St. Charles, Mo., USA); ELISA for free fatty acids (WAKO chemicals, Richmond, Va., USA), and IL-6 and VCAM-1 (R&D Systems, Minneapolis, Minn., USA). CRP was analysed by immunoturbidometry (WAKO chemicals, Richmond, Va., USA), Salicylate levels were assessed commercially using a colorimetric assay (Quest Laboratories, Cambridge, Mass., USA). Glycated albumin was evaluated with the use of a Hitachi 911 lipid and protein analyzer and kits from AsahiKasei (Tokyo, JP). Glycated albumin was calculated by determining (1) the colorimetric measurement of total, albumin; (2) partial enzymatic digestion of albumin at glycated sites; (3) re-assessment of albumin; (4) % glycated albumin=1-3.

Statistical Analysis

The primary endpoint was change from, baseline in glycemic measures using between group comparisons. Secondary outcomes were also assessed as change from baseline within group. Data are presented as mean±standard error unless otherwise noted. Unpaired (salsalate vs. placebo) and paired (pre vs. post) Student t-tests were performed. Treatment effects were determined by calculating differences between baseline sad end of treatment values divided by the baseline value to determine a percent change for each participant. Repeated measures of ANOVA and area under curve analyses were performed to compare response to oral glucose load before and after treatment. Only subjects completing the trial were included in data analysis. Results were considered significant with two-tailed p-values <0.05.

Results

Figure 1A:
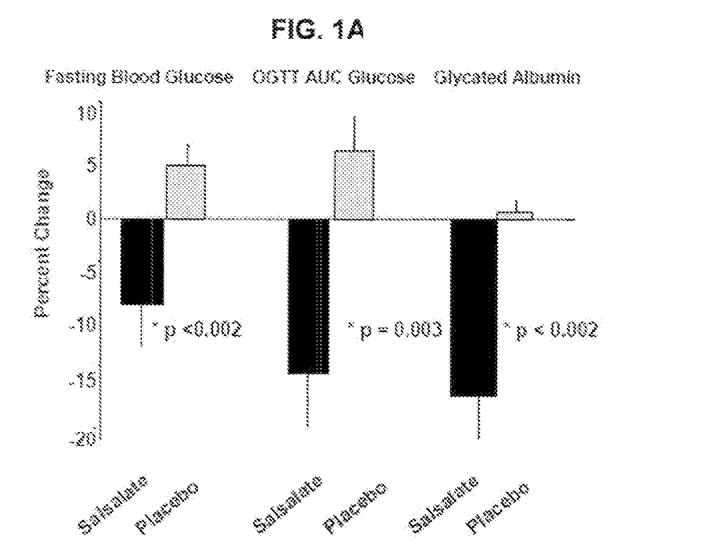
Figure 1B:
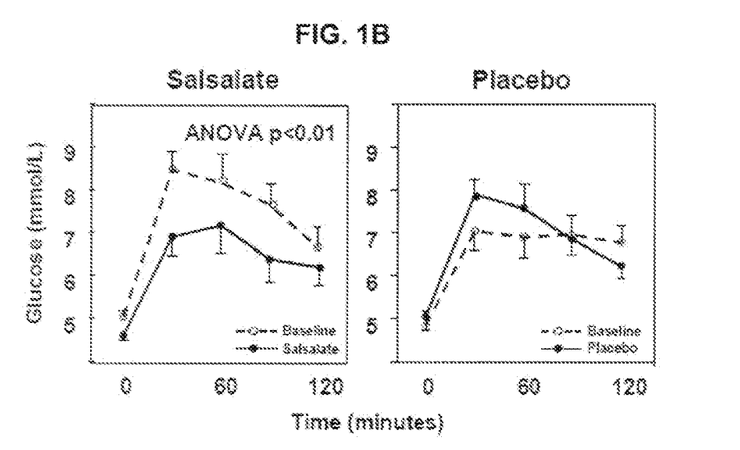
FIG. 1B is a pair of line graphs Illustrating improvements in glycemia in the salsalate treated group (left graph) post oral glucose challenge, illustrated by within group ANOVA analysis and when compared to the placebo treated group (right group). Mean and standard error data for the oral glucose tolerance test are demonstrated before and 30, 60, 90, and 120 minutes following 75 g oral glucose. Baseline data is depicted by the dashed line and open circle, and post treatment data by the solid line and closed circle.

The change in fasting glucose from baseline between salsalate and placebo groups was highly significant alter one mouth: with a reduction of 8±4% following salsalate, compared to an increase of 5±2% following placebo (p<0.002) (FIG. 1a, left). Likewise, glucose area under the curve during oral glucose tolerance testing was reduced by 14±5% after salsalate and increased by 6±3% following placebo for a highly significant improvement from baseline in between group analysis (p=0.003) (FIG. 1A, middle). In addition, the glycated albumin was reduced by 17±4% salsalate compared to 0.6±0.9% after placebo (p<0.002) (FIG. 1A, right). Thus in between group analyses, multiple measures of glycemia improved in salsalate compared to placebo treated groups. Within group comparisons also demonstrated improvement following salsalate, but not placebo. The glycemia response to glucose load improved following salsalate treatment (repeated measure analysis p<0.01), but not placebo daring the one-month study (FIG. 1B), Within groups, one mouth of salsalate resulted in a significant reduction in fasting plasma glucose level from 5.0±0.2 to 4.6±0.1 mmol/L (p<0.03), whereas subjects receiving placebo had a non-significant increase in fasting plasma glucose from 4.8±0.1 to 5.1±0.1 mmol/L (p=0.1). Finally, glycated albumin decreased following salsalate from 12.4±0.4% to 10.3±0.3% (p<0.003) but was unchanged following placebo 12.5±0.3% to 12.4±0.4% (p=0.5). Therefore, glycemia, assessed by fasting, post-glucose load and glycated albumin, was significantly reduced following salsalate when compared to a placebo treated group. No symptomatic hypoglycemia was noted in either group.

Figure 2A:
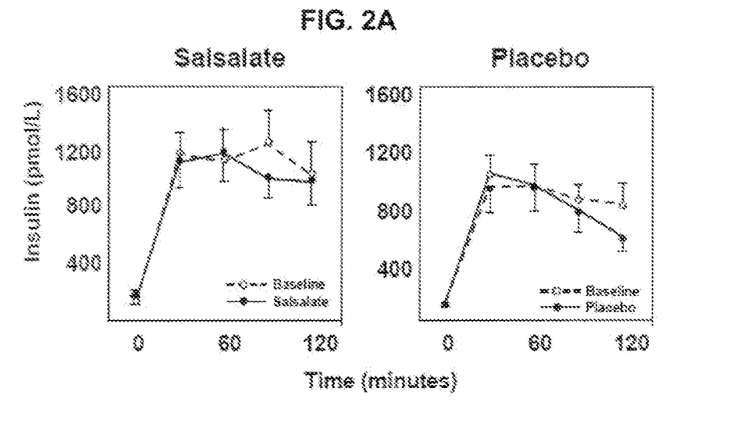
FIGS. 2A and 2B are both pairs of bar graphs illustrating insulin, C-peptide and insulin sensitivity in salsalate treated (left graphs) and placebo treated (right graphs) subjects. Mean and standard error data are demonstrated before and 30, 60, 90 and 120 minutes following 75 g oral glucose for insulin (2A) and C-peptide (2B). Baseline data is depicted by the dashed line and open circle, and post treatment data by the solid line and closed circle.
Figure 2B:
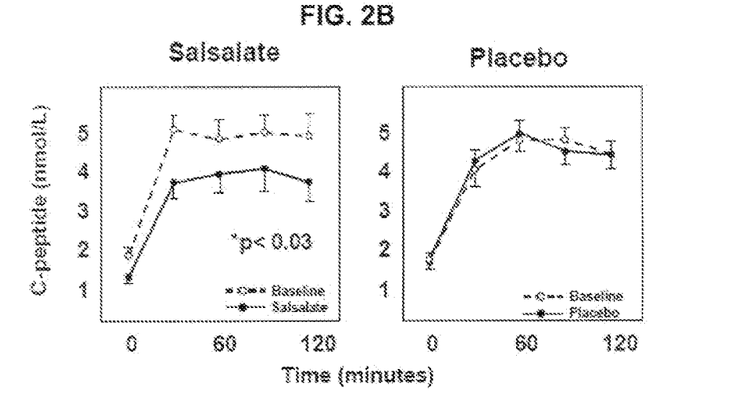
Figure 2C:
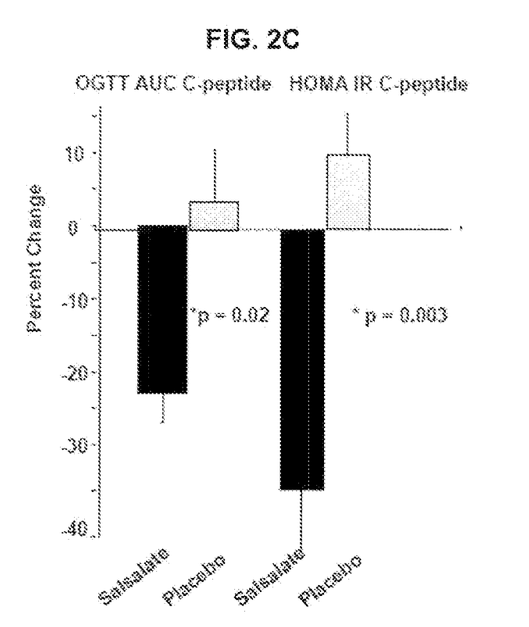
FIG. 2C is a bar graph showing that the C peptide response to Oral Glucose Tolerance Test calculated by AUG showed a significant between group difference. Insulin sensitivity calculated by HOMA IRc-peptide showed a significant difference between group difference with improvement in the salsalate compared to the placebo treated group. Black bar salsalate. Grey bar=placebo.

Fasting insulin values were unchanged in both groups. Similarly, insulin levels following glucose challenge remained unchanged pre- and post-salsalate and placebo exposure (FIG. 2A). However, the change in fasting C-peptide between salsalate and placebo treated groups was highly significant, with a reduction of 30±7% following salsalate and increase of 5±6% following placebo (p<0.01). Within groups, fasting C-peptide levels decreased following salsalate from 1.6±0.2 to 1.1±0.2 nmol/L (p=0.02), but remained unchanged following placebo from 1.5±0.2 to 1.5±0.2 nmol/L (p=0.5). The change in C-peptide AUC post glucose challenge was also significantly different between groups with a reduction of 23±4% following salsalate and increase of 4±7% following placebo (p=0.02) (FIGS. 2B and 2c, left).

Salicylates have previously been demonstrated to reduce insulin clearance (Hundal et al., Clin. Invest. 109:1321-1326 (2002). Taken together, these data suggest improved insulin sensitivity as further supported by homeostasis model assessment of insulin resistance calculated using C-peptide rather than insulin (HOMA IRc peptide), which was significantly lowered by 35±8% in the treatment group and increased 9±5% following placebo (p=0.003) (FIG. 2C, right). However, HOMA-IR using insulin was not significantly changed in either grotto: salsalate 4.6±0.9 vs. 4.2±0.6 (p=0.9) and placebo 3.5±0.5 vs. 3.5±0.5 (p=0.7), pre vs. post treatment, respectively, with no difference in the change between groups (p=0.7). These findings are consistent with reduced insulin clearance and improved insulin sensitivity contributing to the improved glycemia.

Example 2

Salicylates Improve Inflammation in Obese Non-Diabetic Young Adults

To evaluate the proposed anti-inflammatory mechanism of action for improvement in glycemia, cytokines and adipokines were assessed pre- and post-one month of therapy in the same population described in Example 1.

Figure 3A:
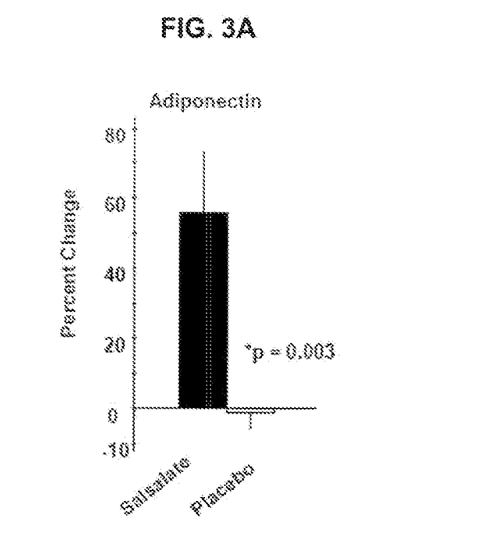
FIG. 3A is a bar graph showing that adiponectin increased significantly in the salsalate treated group when compared to foe placebo group. Black bar=salsalate, Grey bar=placebo.
Figure 3B:
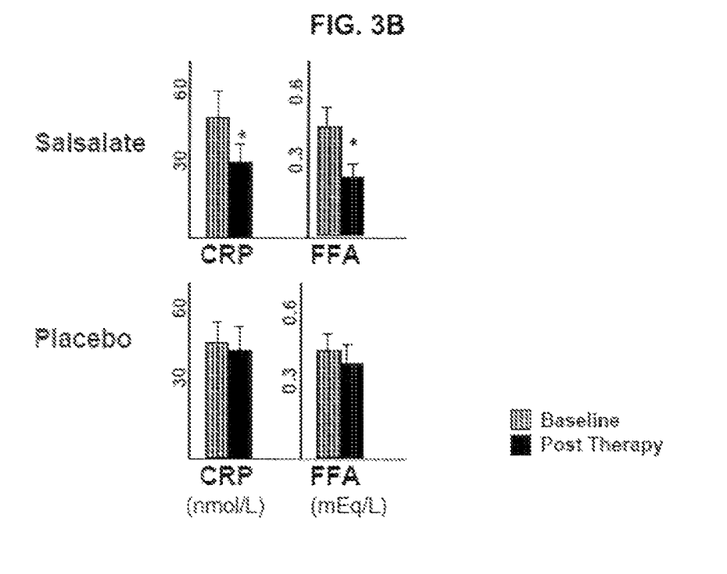
FIG. 3B is a bar graph showing that C-reactive protein (CRP) and Free Fatty Acids (FFA) were lower following salsalate treatment, but unchanged following placebo. (*=p< 0.05). Dotted bar=baseline, Black bar=post therapy

Importantly, inflammatory markers also showed significant improvement following salsalate when compared to the placebo treated group, Adiponectin increased 56±17% in the treatment group and decreased 1±5% in the placebo group (p=0.003), consistent with improved insulin sensitivity (FIG. 3A). In the within group analysis, adiponectin showed a significant increase in the treatment group (10.6±1.7 vs. 16.2±2.7 mg/L, p=0.01), and was unchanged with placebo (10.8±1.5 vs. 10.5±1.5 mg/L, p=0.5). In change from baseline analysis, CRT concentrations decreased from 48.2±10.5 to 30.2±7.4 nmol/L (p=0.05) following salsalsate, without a significant change following placebo from 45.4±8.4 to 42.7±9.6 nmol/L (p=0.7) (FIG. 3B, left), and lasting nonesterified fatty acids (FFA) levels showed a decline following salsalate from 0.46±0.08 to 0.25±0.05 mEq/L (p=0.05) with no change following placebo, from 0.45±0.07 to 0.39±0.09 mEq/L (p=0.6) (FIG. 3B, right), although the between group comparison did not reach statistical significance. Additional inflammatory markers II-6 and soluble VCAM-1 did not change significantly following salsalate therapy.

The data support the hypothesis that subacute chronic inflammation contributes to the pathogenesis of obesity related insulin resistance and early dysglycemia, and suggest that inhibition of inflammation by salsalate provides a novel therapeutic route for diabetes prevention.

Example 3

Safety and Tolerability of Salicylates

All of the subjects described in Example 1 were initialed on 4.0 grams/day of salsalate or placebo given orally, divided in two equal doses. Three participants required dose reduction due to complaints of tinnitus, headache or dizziness. Two of the three participants were on study medication while one was on placebo. All participants completed the trial on the reduced dose. Of the actively treated participants, one tolerated 3.5 grams per day and one tolerated 3.0 grams per day without symptoms.

Salicylates are known to cause anion gap acidosis and NSAIDs as a medication, class have been associated with alterations in renal sanction. There were no noted changes in laboratory analysis of renal function, electrolytes, or anion gap during this trial. Although salsalate has a rare reported prevalence of allergic reactions (Atkinson, Clin Ther 17:827-837 (1995), Stevenson et al., J. Allergy. Clin. Immunol. 86:749-758 (1990)), three participants who received active therapy were withdrawn due to a rash that developed while on therapy. No respiratory distress was noted. Although there was no statistically significant change in meat alanine aminotransferase (ALT) and aspartate aminotransferase (AST) over the one-month period in the treatment or placebo groups (p>0.1), two actively treated participants were noted to have transient mild transaminitis at the final, visit. One participant had an isolated rise in ALT to less than twice the upper range of normal, and a second participant had a similarly mild elevation in both ALT and AST. Both resolved spontaneously.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of improving glycemic control, in a subject with a body mass index (BMI) of $\geq 25$, the method comprising determining whether the subject has a BMI of $\geq 25$, and if the subject has a BMI of $\geq 25$, then administering to the subject a therapeutically effective amount of a non-acetylated form of salicylate, thereby improving glycemic control in the subject wherein, at the time of administration of one or more of the first, second, or third dose of a non-acetylated form of salicylate, the subject is not being treated for diabetes.

2. A method of improving glycemic control in a subject who has metabolic syndrome, the method comprising determining whether the subject has metabolic syndrome, and if the subject has metabolic syndrome, then administering to the subject a therapeutically effective amount of a non-acetylated form of salicylate, thereby improving glycemic control in the subject.

3. The method of claim 1, wherein the subject is selected based on one or more of the following criteria:
the subject is at risk for T2D;
the subject has a Fasting Glucose levels of 100-125;
the subject has a 2-Hour Plasma Glucose Result in a Oral Glucose Tolerance Test of 140-198 mg/dL; or
the patient has a BMI of $\geq 25$;
then the patient is selected for treatment for improving glycemic control with a non-acetylated form of salicylate.

4. The method of claim 1, further comprising informing the subject that the purpose of the treatment is for improving glycemic control.

5. The method of claim 1, further comprising testing the subject for T2D after treatment with a non-acetylated form of salicylate to improve glycemic control, and optionally if the patient develops T2D, administering a drug to treat T2D, wherein the drug is other than a non-acetylated form of salicylate.

6. The method of claim 1, comprising determining whether the subject has a BMI of $\geq 30$, and if the subject has a BMI $\geq 30$, then administering to the subject a therapeutically effective amount of a non-acetylated form of salicylate, thereby improving glycemic control in the subject.

7. The method of claim 1, wherein the non-acetylated form of salicylate is salsalate or trilisate.

8. The method of claim 1, wherein the therapeutically effective amount of a non-acetylated form of salicylate is 3-4.5 g/day.

9. A method of improving glycemic control, in a subject with a body mass index (BMI) of $\geq 25$, the method comprising determining whether the subject has a BMI of $\geq 25$, and if the subject has a BMI of $\geq 25$, then administering to the subject a therapeutically effective amount of a non-acetylated form of salicylate, thereby improving glycemic control in the subject, wherein the subject is not suffering from pain.

10. The method of claim 9, wherein the subject is not being administered a non-acetylated form of salicylate for the treatment of pain.

11. The method of claim 1, wherein determining whether the subject has a BMI of $\geq 25$ includes determining the subject's weight, determining the subject's height, and calculating the subject's BMI using the subject's weight and height in the following formula:

$$\text{weight in kilograms divided by height in meters squared } (BMI=\text{kg/m}^2).$$

12. The method of claim 2, wherein determining whether the subject has metabolic syndrome comprises determining whether the subject has at least three of the following: abdominal obesity, fasting blood triglycerides, low blood HDL, high blood pressure, and elevated fasting glucose.

13. The method of claim 1, further comprising determining whether the subject has T2D, and if determination indicates that the subject does not have T2D, then administering a therapeutically effective amount of a non-acetylated form of salicylate.

14. The method of claim 13, wherein determining whether the subject has T2D comprises administering one or more of a Fasting Plasma Glucose Test, wherein a result of 125 mg/dL or more indicates that the subject has T2D; and a 2-Hour Plasma Glucose Result in a Oral Glucose Tolerance Test, wherein a result of 199 mg/dL or indicates that the subject has T2D; and a blood glucose test, wherein a level of more than 200 mg/dL indicates that the subject has T2D.

15. The method of claim 2, wherein the subject is selected based on one or more of the following criteria:
the subject is at risk for T2D;
the subject has a Fasting Glucose levels of 100-125;
the subject has a 2-Hour Plasma Glucose Result in a Oral Glucose Tolerance Test of 140-198 mg/dL; or the patient has a BMI of ≧25;
then the patient is selected for treatment for improving glycemic control with a non-acetylated form of salicylate.

16. The method of claim 2, further comprising informing the subject that the purpose of the treatment is for improving glycemic control.

17. The method of claim 2, wherein, at the time of administration of one or more of the first, second, or third dose of a non-acetylated form of salicylate, the subject is not being treated for diabetes.

18. The method of claim 2, further comprising testing the subject for T2D after treatment with a non-acetylated form of salicylate to improve glycemic control, and optionally if the patient develops T2D, administering a drug to treat T2D, wherein the drug is other than a non-acetylated form of salicylate.

19. The method of claim 2, wherein the non-acetylated form of salicylate is salsalate or trilisate.

20. The method of claim 2, wherein the therapeutically effective amount of a nonacetylated form of salicylate is 3-4.5 g/day.

21. The method of claim 2, wherein the subject is not being administered a nonacetylated form of salicylate for the treatment of pain.

22. The method of claim 2, further comprising determining whether the subject has T2D, and if determination indicates that the subject does not have T2D, then administering a therapeutically effective amount of a non-acetylated form of salicylate.

23. The method of claim 22, wherein determining whether the subject has T2D comprises administering one or more of a Fasting Plasma Glucose Test, wherein a result of 125 mg/dL or more indicates that the subject has T2D; and a 2-Hour Plasma Glucose Result in a Oral Glucose Tolerance Test, wherein a result of 199 mg/dL indicates that the subject has T2D; and a blood glucose test, wherein a level of more than 200 mg/dL indicates that the subject has T2D.

24. A method of reducing risk of developing type 2 diabetes (T2D) or delaying the development of T2D, in a subject with a body mass index (BMI) of ≧25, the method comprising determining whether the subject has a BMI of ≧25, and if the subject has a BMI of ≧25, then administering to the subject a therapeutically effective amount of salsalate or trilisate, thereby reducing risk of developing T2D or delaying the development of T2D in the subject.

25. A method of reducing risk of developing type 2 diabetes (T2D) or delaying the development of T2D in a subject who has metabolic syndrome, the method comprising determining whether the subject has metabolic syndrome, and if the subject has metabolic syndrome, then administering to the subject a therapeutically effective amount of salsalate or trilisate, thereby reducing risk of developing T2D or delaying the development of T2D in the subject.

\* \* \* \* \*